(12) United States Patent
Tsuda et al.

(10) Patent No.: US 8,067,528 B2
(45) Date of Patent: Nov. 29, 2011

(54) METHOD FOR PRODUCING FLUORINE-CONTAINING POLYMER, AQUEOUS DISPERSION OF FLUORINE-CONTAINING POLYMER, 2-ACYLOXYCARBOXYLIC ACID DERIVATIVE, AND SURFACE ACTIVE AGENT

(75) Inventors: Nobuhiko Tsuda, Settsu (JP); Yoshihiro Yamamoto, Settsu (JP); Yoshinori Nanba, Settsu (JP); Yasuhiko Sawada, Settsu (JP); Tetsuo Shimizu, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 12/788,214

(22) Filed: May 26, 2010

(65) Prior Publication Data

US 2010/0234635 A1  Sep. 16, 2010

Related U.S. Application Data

(62) Division of application No. 12/494,208, filed on Jun. 29, 2009, now Pat. No. 7,754,796, which is a division of application No. 10/564,642, filed as application No. PCT/JP2004/010214 on Jul. 16, 2004, now Pat. No. 7,569,631.

(30) Foreign Application Priority Data

Jul. 16, 2003 (JP) .................. 2003-275581
Jul. 16, 2003 (JP) .................. 2003-275582

(51) Int. Cl.
*C08G 73/24* (2006.01)
*C08G 63/00* (2006.01)
*C08K 5/09* (2006.01)
*C08K 5/10* (2006.01)
*C08F 14/18* (2006.01)
*C08F 2/26* (2006.01)

(52) U.S. Cl. ........ 528/401; 528/271; 528/272; 524/300; 524/773; 560/179

(58) Field of Classification Search .................. 528/401, 528/271, 272; 524/300, 773; 560/179
See application file for complete search history.

(56) References Cited

U.S. PATENT DOCUMENTS

| 4,529,781 | A | 7/1985 | Cavanaugh |
| 4,564,661 | A | 1/1986 | Beresniewicz |
| 5,182,132 | A | 1/1993 | Murai et al. |
| 5,443,888 | A | 8/1995 | Murai et al. |
| 5,663,251 | A | 9/1997 | Kato et al. |
| 5,763,552 | A | 6/1998 | Feiring et al. |
| 6,103,843 | A | 8/2000 | Abusleme et al. |
| 6,429,258 | B1 | 8/2002 | Morgan et al. |
| 6,437,186 | B1 | 8/2002 | Ostgard et al. |
| 6,482,882 | B2 | 11/2002 | Abusleme et al. |
| 6,858,573 | B1 | 2/2005 | Grade et al. |
| 2001/0020064 | A1 | 9/2001 | Ishikawa et al. |
| 2002/0137970 | A1 | 9/2002 | Ostgard et al. |

FOREIGN PATENT DOCUMENTS

| EP | 0021739 A1 | 1/1981 |
| EP | 0191605 A2 | 8/1986 |
| EP | 0432536 A2 | 6/1991 |
| EP | 0473871 A2 | 3/1992 |
| JP | 60188408 | 9/1985 |
| JP | 61207413 | 9/1986 |
| JP | 60228008 | 10/1986 |
| JP | 61286348 | 12/1986 |
| JP | 3224132 | 10/1991 |
| JP | 710909 | 1/1995 |
| JP | 8333408 | 12/1996 |
| JP | 9183880 | 7/1997 |
| JP | 10212261 | 8/1998 |
| JP | 11228501 | 8/1999 |
| JP | 2001226439 | 8/2001 |
| JP | 2002226439 | 8/2002 |
| JP | 2002234860 | 8/2002 |
| JP | 2002308914 A | 10/2002 |
| JP | 2003119204 | 4/2003 |
| JP | 2006513303 | 4/2006 |
| WO | 9820055 A1 | 5/1998 |
| WO | 02059159 A1 | 8/2002 |
| WO | 2004067588 A1 | 8/2004 |

OTHER PUBLICATIONS

Maria Iorio, et al.; "Synthesis of colchifoline from deacetylcolchiceine," Canadian Journal of Chemistry, 1981, 59 (2), pp. 283-284.

Osipov, et al.; "A new strategy for the synthesis of a-difluoromethyl-substituted a-hydroxy and a-amino acids," Journal of Organic Chemistry, 1996, 61 (21), pp. 7521-7528.

*Primary Examiner* — Duc Truong

(74) *Attorney, Agent, or Firm* — Sughrue Mion, PLLC

(57) ABSTRACT

The present invention provides a method of producing a fluoropolymer, wherein polymerization using a carboxylate ester bond-containing carboxylic acid derivative as a surfactant in an aqueous medium to give the fluoropolymer is conducted, the above carboxylate ester bond-containing carboxylic acid derivative has a carboxylate ester bond and —COOM (M representing H, $NH_4$, Li, Na or K), the above carboxylate ester bond may optionally be substituted by fluorine atom.

6 Claims, No Drawings

METHOD FOR PRODUCING FLUORINE-CONTAINING POLYMER, AQUEOUS DISPERSION OF FLUORINE-CONTAINING POLYMER, 2-ACYLOXYCARBOXYLIC ACID DERIVATIVE, AND SURFACE ACTIVE AGENT

CROSS REFERENCE TO THE RELATED APPLICATIONS

This application is a Divisional of U.S. patent application Ser. No. 12/494,208 filed Jun. 29, 2009 now U.S. Pat. No. 7,754,796, which is a Divisional of U.S. patent application Ser. No. 10/564,642 now U.S. Pat. No. 7,569,631, which is a 371 of PCT Application No. PCT/JP2004/010214 filed Jul. 16, 2004 and which claims benefit of JPA No. 2003-275581 filed Jul. 16, 2003 and JPA No. 2003-275582 filed Jul. 16, 2003. The above-noted applications are incorporated herein by reference in their entirety.

TECHNICAL FIELD

The present invention relates to a method of producing a fluoropolymer, a fluoropolymer aqueous dispersion, a 2-acyloxycarboxylic acid derivative, and a surfactant.

BACKGROUND ART

A number of documents describe, as a method of producing fluoropolymers, the method of polymerizing tetrafluoroethylene [TFE] in an aqueous medium using, as a surfactant, a straight or partially branched fluorine-substituted carboxylic acid containing 7 to 10 carbon atoms (cf. e.g. Patent Document 1, Patent Document 2 and Patent Document 3).

A method of producing fluoropolymers which uses a carboxylic acid containing a fluorinated polyoxyalkylene group as a surfactant has also been disclosed (cf. e.g. Patent Document 4).

However, while those surfactants are thermally and chemically very stable and they are useful on the occasion of polymerization because of their being capable of preventing side reactions such as chain transfer, they have a problem, namely the washing, heating and other conditions in removing them from the resins obtained by polymerization are narrowly restricted.

A method of producing fluoropolymers which uses a sulfosuccinic acid ester as a surfactant has been disclosed (cf. e.g. Patent Document 5). However, the sulfosuccinic acid ester has problems: it is difficult to remove the same from the resin by heating, for instance, and, when it remains in the resin, they cause problems, for example discoloration after heating or a like processing.

Meanwhile, there are known, as fluoro-2-hydroxycarboxylic acid esters, hydroxycarboxylic acid esters $[(CF_3)_2C(OH)COOR$ (in which R represents a hydrocarbon group) obtained by oxidation, with $KMnO_4$, of heptafluoroisobutenyl alkyl ethers $[(CF_3)_2]C=CFOR]$, which are obtainable starting with octafluoroisobutene formed as a byproduct in the production of hexafluoropropene (cf. e.g. Non-Patent Document 1). However, the treatment of the byproduct $MnO_2$ formed from $KMnO_4$ is troublesome.

Also known is the $H_2O_2$ method which comprises oxidizing $(CF_3)_2C=CFOR$ with $H_2O_2$ in lieu of $KMnO_4$ (cf. e.g. Patent Document 6). However, the $H_2O_2$ method has problems; for example, the yield is low.

Further known as fluoro-2-hydroxycarboxylic acid esters are compounds of the formula $[CF_3(CF_2)_{k1}][CF_3](CF_2)_{k2}]C(OH)COOR$ (in which R represents a hydrocarbon group; and k1 and k2 each represents an integer of 0 to 10) obtained by oxidation, in the presence of a ruthenium compound or osmium compound, of compounds represented by the formula $[(CF_3)(CF_2)_{k1}][CF_3](CF_2)_{k2}]C=CF(OR)$ (cf. e.g. Patent Document 7). It is also known that fluoro-2-hydroxycarboxylic acids can be derived from the above fluoro-2-hydroxycarboxylic acid esters (cf. e.g. Patent Document 7).

However, those ester compounds which result from introduction of an acyl group into the OH group of those fluoro-2-hydroxycarboxylic acids are unknown.

Patent Document 1: Japanese Kokai Publication S61-207413
Patent Document 2: Japanese Kokai Publication S61-228008
Patent Document 3: Japanese Kokai Publication H10-212261
Patent Document 4: U.S. Pat. No. 6,429,258
Patent Document 5: Japanese Kokai Publication 2003-119204
Patent Document 6: Japanese Kokai Publication S61-286348 (claim 1)
Patent Document 7: Japanese Kokai Publication 2002-234860 (claim 1)
Non-Patent Document 1: Utebaev U. et al.: Izv. Akad. Nauk SSSR Ser. Khim., 2 (1974) 387

DISCLOSURE OF THE INVENTION

Problems which the Invention is to Solve

In view of the above-discussed state of the art, it is an object of the present invention to provide a method of producing fluoropolymers in an aqueous medium using a surfactant whose stability will not be impaired in the step of polymerization and whose residual content in fluoropolymer particles after such processing as coagulation/flocculation is very low, and a fluoropolymer aqueous dispersion in which use is made of a surfactant which can provide fluoropolymers with excellent dispersion stability and whose residual content in fluoropolymer particles after such processing as coagulation/flocculation is very low.

Another object of the invention is to provide a 2-acyloxycarboxylic acid derivative as well as a surfactant comprising the 2-acyloxycarboxylic acid derivative.

Means for Solving the Problems

The present invention provides a method of producing a fluoropolymer, wherein polymerization using a carboxylate ester bond-containing carboxylic acid derivative as a surfactant in an aqueous medium to give the fluoropolymer is conducted, the above carboxylate ester bond-containing carboxylic acid derivative has a carboxylate ester bond and —COOM (M representing H, $NH_4$, Li, Na or K), the above carboxylate ester bond may optionally be substituted by fluorine atom.

The invention also provides a fluoropolymer aqueous dispersion which comprises a particle comprising a fluoropolymer, a carboxylate ester bond-containing carboxylic acid derivative and an aqueous medium, wherein the above carboxylate ester bond-containing carboxylic acid derivative has a carboxylate ester bond and —COOM (M representing H, $NH_4$, Li, Na or K), the above carboxylate ester bond may optionally be substituted by fluorine atom.

The invention further provides a 2-acyloxycarboxylic acid derivative which is represented by the general formula (1):

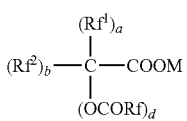
(1)

wherein $Rf^1$ and $Rf^2$ are the same or different and each represents H, F, a fluoroalkyl group containing 1 to 20 carbon atoms or an ether oxygen-containing fluoroalkyl group containing 1 to 20 carbon atoms, Rf represents a fluoroalkyl group containing 1 to 20 carbon atoms or an ether oxygen-containing fluoroalkyl group containing 1 to 20 carbon atoms, M represents H, NH4, Li, Na or K, a and b each represents an integer of 0 to 2 and d represents an integer of 1 to 3 provided that a, b and d satisfy the relation a+b+d=3; $Rf^1$, $Rf^2$ and Rf are the same or different.

The invention further provides a surfactant which comprises the above 2-acyloxycarboxylic acid derivative.

The invention still further provides a method of producing a 2-acyloxycarboxylic acid derivative, which comprises producing the above 2-acyloxycarboxylic acid by esterifying a 2-hydroxycarboxylic acid derivative represented by the general formula (5):

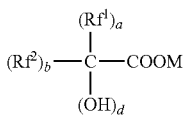
(5)

wherein $Rf^1$ and $Rf^2$ are the same or different and each represents H, F, a fluoroalkyl group containing 1 to 20 carbon atoms or an ether oxygen-containing fluoroalkyl group containing 1 to 20 carbon atoms, M represents H, $NH_4$, Li, Na or K, a and b each represents an integer of 0 to 2 and d represents an integer of 1 to 3 provided that a, b and d satisfy the relation a+b+d=3, and an alkanoyl compound represented by the general formula (6):

RfCOZ (6)

wherein Rf represents a fluoroalkyl group containing 1 to 20 carbon atoms or an ether oxygen-containing fluoroalkyl group containing 1 to 20 carbon atoms, Z represents —$OM^1$ or Y ($M^1$ representing H, $NH_4$, Li, Na or K and Y representing F or Cl).

In the following, the present invention is described in detail.

The method of producing a fluoropolymer of the invention comprises polymerization using a carboxylate ester-containing carboxylic acid derivative as a surfactant in an aqueous medium to give the fluoropolymer.

The above-mentioned "fluoropolymer" is a polymer containing carbon atom-bound fluorine atoms. In the practice of the invention, the fluoropolymer is obtained by polymerizing one or two or more fluorine-containing monomers, optionally together with a fluorine-free monomer(s) containing no fluorine atom for copolymerization. The "fluorine-containing monomer" is a monomer containing at least one carbon atom-bound fluorine atom. The fluoropolymer will be described in detail later herein.

The carboxylate ester bond-containing carboxylic acid derivative mentioned above is a carboxylic acid derivative having a carboxylate ester bond and —COOM (M being as defined above).

The term "carboxylate ester bond" as used herein means a structure resulting from bonding between (1) —COO— or or —OCO— and (2) a hydrocarbon group one or more hydrogen atoms of which may optionally be substituted by fluorine atoms or other substituents and which may optionally contain an ether oxygen atom(s) in the principal chain thereof. As the above carboxylate ester bond, there may be mentioned, for example, a structure represented by R—COO—, and a structure represented by R—OCO— (R representing an alkyl group, which may optionally be substituted by a substituent, or the above-mentioned ether oxygen-containing fluoroalkyl group, which may optionally be substituted by a substituent).

The carboxylate ester bond-containing carboxylic acid derivative mentioned above, when subjected to such after-treatment as coagulation/flocculation after the above-mentioned polymerization, readily undergoes ester hydrolysis, and the hydrolysis product formed is generally volatile and can be removed by heating.

The carboxylate ester bond is preferably an acyloxy group represented by RfCOO— (Rf representing a fluoroalkyl group containing 1 to 20 carbon atoms or an ether oxygen-containing fluoroalkyl group containing 1 to 20 carbon atoms) or an alkoxycarbonyl group represented by RfOCO— (Rf being as defined above).

The term "fluoroalkyl group" as used herein means an alkyl group at least one H has been substituted by F.

The term "ether oxygen-containing fluoroalkyl group" as used herein means an alkyl group which contains an alkyleneoxy group containing 1 to 3 carbon atoms as a repeating unit in the principal chain thereof and at least one H of which has been substituted by F.

As the ether oxygen-containing fluoroalkyl group, there may be mentioned, among others, —$(CF_2O)_k$—, —$(CH_2CF_2O)_k$—, —$(CF_2CF_2O)_k$—, —$(CF(CF_3)CF_2O)_k$—, and combinations of these, for example —$(CF_2CF_2O)_k$—$(CF(CF_3)CF_2O)_k$— (the symbols k's being the same or different and each being an integer such that the number of carbon atoms in the respective ether oxygen-containing fluoroalkyl group amounts to 1 to 20).

The "ether oxygen-containing fluoroalkyl group" so referred to herein differs from the above-mentioned "fluoroalkyl group" in that it contains an ether oxygen atom or atoms, as mentioned above.

In cases where the group Rf is the above-mentioned fluoroalkyl group, a preferred lower limit to the number of carbon atoms is 2, a more preferred lower limit is 3, a preferred upper limit is 9, and a more preferred upper limit is 4.

In cases where the group Rf is the above-mentioned ether oxygen-containing fluoroalkyl group, a preferred lower limit to the number of carbon atoms is 2, a preferred upper limit is 8, and a more preferred upper limit is 4.

As regards the above M in the carboxylate ester bond-containing carboxylic acid derivative, $NH_4$ is preferred from the viewpoint of ready eliminability from the fluoropolymers formed by means of heating treatment, while Li, Na and K are preferred from the emulsifying or dispersing power viewpoint.

Preferred as the carboxylate ester bond-containing carboxylic acid derivative to be used in the method of producing a fluoropolymer according to the invention are, among others: 2-acyloxycarboxylic acid derivatives represented by the general formula (1):

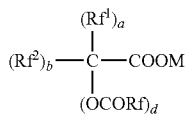   (1)

wherein $Rf^1$ and $Rf^2$ are the same or different and each represents H, F, a fluoroalkyl group containing 1 to 20 carbon atoms or an ether oxygen-containing fluoroalkyl group containing 1 to 20 carbon atoms, a and b each represents an integer of 0 to 2 and d represents an integer of 1 to 3 provided that a, b and d satisfy the relation a+b+d=3; Rf and M are as defined above; $Rf^1$, $Rf^2$ and Rf are the same or different, and dicarboxylic acid half esters represented by the general formula (2):

RfOCO—$Rf^3$—COOM     (2)

wherein $Rf^3$ represents an alkylene group containing 1 to 8 principal chain carbon atoms, which may optionally contain one substituent $Rf^4$ and/or one double bond ($Rf^4$ representing F, a fluoroalkyl group containing 1 to 20 carbon atoms or an ether oxygen-containing fluoroalkylene group containing 1 to 20 carbon atoms) and Rf and M are as defined above.

The carboxylate ester bond-containing carboxylic acid derivatives of the general formulas (1) and (2) given above are described in detail in the following.

2-Acyloxycarboxylic acid derivatives

As regards the groups $Rf^1$, $Rf^2$ and Rf in the above general formula (1), the number of carbon atoms in each of them, the value of d and so forth may be selected so as to attain the desired surfactant performance characteristics and, further, the number of C—H bonds is preferably selected taking the chain transfer characteristics into consideration since the derivatives in question are to be used as surfactants in producing a fluoropolymer according to the invention. In view of the use of the 2-acyloxycarboxylic acid derivatives in such fields of application where they should not remain after their functioning as such surfactants as mentioned above, it is particularly important that the number of carbon atoms in each group should not be so excessive that the volatility of the hydrolysis product mentioned above may be impaired.

In the above general formula (1), a and b each represents an integer of 0 to 2, and d represents an integer of 1 to 3, provided that a, b and d satisfy the relation a+b+d=3. From the ready preparation viewpoint, d is preferably an integer of 1 to 2, more preferably 1.

In the above general formula (1), $Rf^1$ and $Rf^2$ are the same or different and each represents H, F, a fluoroalkyl group containing 1 to 20 carbon atoms or an ether oxygen-containing fluoroalkyl group containing 1 to 20 carbon atoms.

In the groups $Rf^1$ and $Rf^2$, a preferred upper limit to the number of carbon atoms in the fluoroalkyl group is 9, a more preferred upper limit is 5, a still more preferred upper limit is 3, and a most preferred upper limit is 2.

In the groups $Rf^1$ and $Rf^2$, a preferred upper limit to the number of carbon atoms in the ether oxygen-containing fluoroalkyl group is 8, a more preferred upper limit is 5, and a still more preferred upper limit is 2.

Preferably, the groups $Rf^1$ and $Rf^2$, which are the same or different, each is a group of the general formula:

$A(CF_2)_j(CH_2)_p$— wherein A represents H or F, j represents an integer of 1 to 6 and p represents an integer of 0 to 3.

F is preferred as the above A.

A preferred upper limit to the above-mentioned j is 4, a more preferred upper limit is 3, and a still more preferred upper limit is 2.

A preferred upper limit to the above-mentioned p is 1, and the integer p is more preferably equal to 0 (zero).

More preferably, the groups $Rf^1$ and $Rf^2$, which are the same or different, each is $CF_3$—, $CF_3CF_2$—, $CF_3CF_2CF_2$— or $CF_3CF_2CF_2CF_2$—.

In the general formula (1), Rf is as defined above.

The term "acyl" as used herein in the phrase "2-acyloxycarboxylic acid derivatives" means the group —CORf, as is evident in view of the general formula (1), and includes, within the meaning thereof, those containing the above-mentioned ether oxygen-containing fluoroalkyl group as well, in accordance with the definition of Rf as given hereinabove.

In the group Rf, a preferred lower limit to the number of carbon atoms in the fluoroalkyl group is 2, a more preferred lower limit is 3, a preferred upper limit is 9, and a more preferred upper limit is 4.

In the group Rf, a preferred lower limit to the number of carbon atoms in the ether oxygen-containing fluoroalkyl group is 2, a preferred upper limit is 8, and a more preferred upper limit is 4.

The group Rf is preferably $A(CF_2)_n(CH_2)_m$— wherein A is as defined above, n represents an integer of 1 to 4 and m represents an integer of 0 to 3, or $A(CF_2)_q$—O—$[CFX$—$CF_2(CH_2)_r O]_t CFX$— wherein X represents F or $CF_3$, q represents an integer of 0 to 3, r represents an integer of 0 to 2, t represents an integer of 0 to 3 and A is as defined above.

The upper limit to the integer n is more preferably 3, and the upper limit to the integer q is more preferably 2.

Preferably, the integers m, r and t are respectively equal to 0 (zero).

The group Rf is more preferably $CF_3$—, $CF_3CF_2$—, $CF_3CF_2CF_2$—. $CF_3CF_2CF_2CF_2$—, $HCF_2$—, $HCF_2CF_2$—, $HCF_2CF_2CF_2$— or $HCF_2CF_2CF_2CF_2$—.

In the above general formula (1), $Rf^1$, $Rf^2$ and $Rf^1$ are the same or different.

When d in the general formula (1) represents an integer of 2 or 3, d groups of Rf are the same or different. When a is 2, a groups of $Rf^1$ are the same or different and, when b is 2, b groups of $Rf^2$ are the same or different.

In preferred examples, $Rf^1$ and $Rf^2$ in the above general formula (1), which are the same or different, each is $A(CF_2)_u$— wherein A is as defined above and u represents an integer of 1 to 3, and Rf is $A(CF_2)_w(CH_2)_y$— wherein A is as defined above, w represents an integer of 2 to 4 and y represents an integer of 0 to 1.

In the above general formula (1), M is as defined above. $NH_4$ is preferred as M because of the possibility of ready elimination, by heating treatment, of the derivatives in question after use as surfactants.

Preferred as the derivatives of general formula (1) in view of the surfactant activity and hydrolyzate volatility are, among others, the following:
$(CF_3)_2C(OCOCF_2CF_2CF_2CF_3)COOM$,
$(CF_3)(CF_3CF_2)C(OCOCF_2CF_2CF_2CF_3)COON$,
$(CF_3CF_2)_2C(OCOCF_2CF_2CF_2CF_3)COOM$,
$(CF_3)C(OCOCF_2CF_2CF_2CF_3)_2COOM$ (CF$_3$CF$_2$)C(OCOCF$_2$CF$_2$CF$_3$)$_2$COOM
(CF$_3$)C(OCOCF$_2$CF$_2$CF$_3$)$_2$COOM,
(CF$_2$CF$_2$)C(OCOCF$_2$CF$_2$CF$_3$)$_2$COOM,
(CF$_3$)C(OCOCF$_2$CF$_3$)$_2$COOM,
(CF$_3$CF$_2$)C(OCOCF$_2$CF$_3$)$_2$COOM,
(CF$_3$)C(OCOCF$_2$CF$_3$)(OCOCF$_2$CF$_2$CF$_3$)COOM,
(CF$_3$)C(OCOCF$_2$CF$_3$) (OCOCF$_2$CF$_2$CF$_3$)COOM,
(CF$_3$)C(OCOCF$_2$CF$_2$CF$_3$)(OCOCF$_2$CF$_2$CF$_3$)COOM,
(CF$_3$CF$_2$)C(OCOCF$_2$CF$_3$)(OCOCF$_2$CF$_2$CF$_3$)COOM,
(CF$_3$CF$_2$)C(OCOCF$_2$CF$_3$)(OCOCF$_2$CF$_2$CF$_3$)$_2$COOM and
(CF$_3$CF$_2$)C(OCOCF$_2$CF$_2$CF$_3$)(OCOCF$_2$CF$_2$CF$_3$) COOM,
wherein M is as defined above.

The method of producing the above 2-acyloxycarboxylic acid derivatives will be described later herein in detail.

Dicarboxylic Acid Half Esters

In the general formula (2) given above, Rf$^3$ is preferably —C$_f$H$_{2f}$—, —C$_g$H$_{2g-2}$— or —(CH$_2$)$_h$-T-(CH$_2$)$_i$— (in which f represents an integer of 1 to 6, g represents an integer of 2 to 6, h and i are the same or different and each represents an integer of 0 to 3 and T represents —CRf$^4$=CH—, —CH=CRf$^4$— or —CHRf$^4$— (Rf$^4$ being as defined above).

The dicarboxylic acid half esters represented by the general formula (2) may be either dicarboxylic acid half esters (A) represented by the general formula (3):

RfOCORf$^5$COOM (3)

wherein Rf and M are as defined above and Rf$^5$ is an unsubstituted alkylene group containing 1 to 6 carbon atoms as represented by —C$_f$H$_{2f}$— or —C$_g$H$_{2g-2}$— (f and g being as defined above), or dicarboxylic acid half esters (B) represented by the general formula (4):

RfOCO(CH$_2$)$_h$-T-(CH$_2$)$_i$—COOM (4)

wherein T represents —CRf$^4$=CH—, —CH=CRf$^4$— or —CHRf$^4$— and Rf, M, h, i and Rf$^4$ are as defined above.

As is evident from the above general formula (3) and general formula (4), the dicarboxylic acid half esters (A) contain an unsubstituted alkylene group having no substituent as Rf$^3$ in the general formula (2), and the dicarboxylic acid half esters (B) contain, as Rf$^3$, a substituted alkylene group or substituted alkenylene group having one substituent Rf$^4$ (Rf$^4$ being as defined above).

In the above general formula (3), each of the integers f and g is preferably not higher than 5, more preferably not higher than 2. The integers f and g are the same or different.

In the above general formula (3), the integers f and g are preferably within the above range, since higher numbers of hydrogen atoms in the group Rf$^5$ tend to produce such problems as decreased rates of polymerization and failure to give high molecular weights.

Preferred as the group Rf$^5$ are —CH$_2$—, —CH$_2$CH$_2$—, —CH$_2$CH$_2$CH$_2$CH$_2$—, —CH=CH— and —CH$_2$—CH=CH—CH$_2$—. More preferred are —CH$_2$—, —CH$_2$CH$_2$—, —CH=CH— and —CH$_2$—CH=CH—CH$_2$—.

The dicarboxylic acid half esters (A) can be produced, for example, by subjecting RfOM$^2$ (Rf being as defined above and M$^2$ representing H, NH$_4$, Li, Na or K) and HOOCRf$^5$COOM (Rf$^5$ and M being as defined above) or the acid anhydride thereof to esterification using some or other method known in the art.

Preferred as Rf$^4$ in the above general formula (4) are F, fluoroalkyl groups containing not more than 8 carbon atoms and ether oxygen-containing fluoroalkylene groups containing not more than 8 carbon atoms. More preferred are F, fluoroalkyl groups containing not more than 4 carbon atoms and ether oxygen-containing fluoroalkylene groups containing not more than 4 carbon atoms.

In the above general formula (4), each of the integers h and i is preferably 0 (zero) or 1, more preferably 0 (zero).

The dicarboxylic acid half esters (B) mentioned above are represented by the following formula:

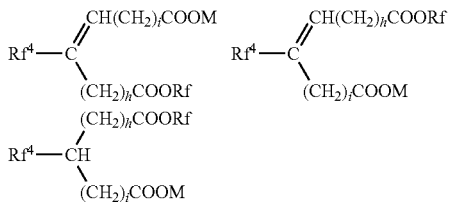

In the above formulas, Rf, Rf$^4$ and M are as defined above, and h and i are the same or different and each represents an integer of 0 to 3.

The dicarboxylic acid half esters (B) can be produced, for example, by reacting M$^3$OOC(CH$_2$)$_h$-T-(CH$_2$)$_i$COOM (M$^3$ representing H, NH$_4$, Li, Na or K and T, M, h and i being as defined above) or the acid anhydride thereof with RfOH(Rf being as defined above) according to some or other method known in the art for half esterification.

In the method of producing a fluoropolymer of the invention, a 0.1% (by mass) aqueous solution of the above-mentioned carboxylate ester bond-containing carboxylic acid derivative preferably has a surface tension of 30 to 70 Nm/m as measured at 25° C. by Wilhelmy method from the surfactant activity viewpoint. A more preferred lower limit to the above surface tension is 40 Nm/m, and a more preferred upper limit is 60 Nm/m.

The carboxylate ester bond-containing carboxylic acid derivatives each remains, together with a fluoropolymer obtained by the polymerization according to the method of producing the fluoropolymer of the present invention, in an aqueous dispersion at a level corresponding to a part or the whole of the usage thereof and, when no change occurs in the environmental conditions causing no substantial hydrolysis, also remains intermingled with the wet powder obtained by coagulation/flocculation of the above-mentioned aqueous dispersion, if desired.

The carboxylate ester bond-containing carboxylic acid derivatives can be recovered after use thereof as surfactants, for instance, for repeated use thereof.

Upon hydrolysis, the carboxylate ester bond-containing carboxylic acid derivatives generally form hydrolyzates. The hydrolysis can be carried out in the presence of an acid or alkali, for instance, mainly in the after-treatment step such as coagulation/flocculation after polymerization by the method of producing fluoropolymers according to the invention. If desired, the hydrolysis may be carried out at a temperature of 10 to 250° C., preferably at 100 to 200° C. The term "hydrolyzates" as used herein means two or more molecular species formed upon hydrolysis, namely a compound containing —COOM (M being as defined above) and RfCOOH (Rf being as defined above) or a salt thereof or RfOH (Rf being as defined above) or an alcoholate thereof. As the salt of RfCOOH, there may be mentioned, for example, RfCOOM (Rf and M being as defined above) and, as the alcoholate, there may be mentioned, for example, RfOM (Rf and M being as defined above).

The carboxylate ester bond-containing carboxylic acid derivatives are preferably such ones that the hydrolyzates thereof are volatile. When the hydrolyzates are volatile, they can be readily eliminated by heating.

The heating includes, among others, the drying or baking after application, to substrates, of a coating composition prepared from the fluoropolymer aqueous dispersion, the drying or pelletization of a wet powder obtained by coagulation/flocculation of the fluoropolymer aqueous dispersion, and the heating in the step of molding or other processing using the dry powder or pellets obtained.

After ordinary after-processing, such as coagulation/flocculation and/or heating, the concentration of the carboxylate ester bond-containing carboxylic acid derivatives can be reduced to a concentration of 10 ppm or lower, preferably 1 ppm or lower, relative to the fluoropolymer aqueous dispersion. Furthermore, on the occasion of such after-treatment as coagulation/flocculation, the washing efficiency can be increased by rendering the fluoropolymer aqueous dispersion acidic or alkaline and carrying out the washing at elevated temperatures.

The carboxylate ester bond-containing carboxylic acid derivatives thus show their surfactant activity as emulsifiers on the occasion of polymerizing a fluoropolymer and, at the same time, they can be removed with ease following after-treatment hydrolysis. Therefore, the method of producing a fluoropolymer according to the invention makes it possible to minimize the contents of the carboxylate ester bond-containing carboxylic acid derivatives coexisting with the fluoropolymer produced and thus makes it possible, for example, to prevent the powders, pellets, moldings, coatings and like materials comprising the fluoropolymer from foaming in the step of processing, improve the physical properties thereof, and prevent them from being discolored during processing.

In the method of producing a fluoropolymer according to the invention, the number of fluorine atom-bound carbon atoms in the above hydrolyzate is preferably not more than 6 from the viewpoint of ready eliminability by heating.

From the above-mentioned eliminability viewpoint, the number of fluorine atom-bound carbon atoms is preferably not smaller than 2 but more preferably not more than 4, still more preferably not more than 3.

In accordance with the method of producing a fluoropolymer according to the invention, it is possible to produce a fluoropolymer efficiently by using at least one of the carboxylate ester bond-containing carboxylic acid derivatives mentioned above as a surfactant. In carrying out the method of producing a fluoropolymer according to the invention, two or more of the carboxylate ester bond-containing carboxylic acid derivatives may be used simultaneously as surfactants, or a certain compound having surfactant activity other than the carboxylate ester bond-containing carboxylic acid derivatives may also be used simultaneously if it is volatile or the remains thereof in fluoropolymer moldings or the like are allowable.

The other compound having surfactant activity is not particularly restricted but may be any of anionic, cationic, nonionic or betaine-type surfactants, for instance, and these surfactants may be hydrocarbon-derived ones.

In the method of producing a fluoropolymer of the invention, an additive for stabilizing each of the carboxylate ester bond-containing carboxylic acid derivatives and the compound having surfactant activity as optionally used may further be used. The additive is not particularly restricted but may be any of those generally used for conventional surfactants, for example stabilizers.

In the method of producing a fluoropolymer of the invention, the polymerization is carried out by charging a polymerization reactor with an aqueous medium, at least one of the carboxylate ester bond-containing carboxylic acid derivatives, a monomer or monomers and, if necessary, another additive, stirring the contents of the reactor, maintaining the reactor at a predetermined polymerization temperature and then adding a predetermined amount of a polymerization initiator to initiate the polymerization reaction. After the start of the polymerization reaction, the same and/or other monomer or monomers, the same or other polymerization initiator, a chain transfer agent, the same or other carboxylate ester bond-containing carboxylic acid derivative and so forth may be supplemented according to the intended purpose.

In the above polymerization, the polymerization temperature is generally 5 to 120° C. and the polymerization pressure is generally 0.05 to 10 MPaG. The polymerization temperature and polymerization pressure are to be appropriately selected according to the monomer species employed, the molecular weight of the desired polymer and the rate of reaction.

One or more of the carboxylate ester bond-containing carboxylic acid derivatives are preferably added at a total addition level of 0.0001 to 15% by mass relative to the aqueous medium, and a more preferred lower limit is 0.001% by mass, a still more preferred upper limit is 10% by mass and a still more preferred upper limit is 1% by mass. At levels lower than 0.0001% by mass, the dispersing power will be insufficient and, at levels exceeding 15% by mass, no more additional effect corresponding to the addition level will be produced but rather the rate of polymerization may decrease or the reaction may terminate in some instances. The level of addition of the carboxylate ester bond-containing carboxylic acid derivatives is to be appropriately selected according to the monomer species employed, the molecular weight of the desired polymer and so forth.

The polymerization initiator is not particularly restricted but may be any of those capable of generating radicals within the polymerization temperature range, including the oil-soluble and/or water-soluble polymerization initiators known in the art. Further, the polymerization may be initiated by using a reducing agent or the like in combination to build up a redox system. The polymerization initiator concentration is to be appropriately selected according to the monomer species employed, the molecular weight of the desired polymer and the rate of reaction.

The "aqueous medium" is a reaction medium in which the polymerization is carried out and means a water-containing liquid. The aqueous medium is not particularly restricted but may be any water-containing one. It may comprise water and a fluorine-free organic solvent, for example an alcohol, ether or ketone, and/or a fluorine-containing organic solvent having a boiling point not higher than 40° C. For example, a fluorine-containing organic solvent such as C318 may be used on the occasion of suspension polymerization.

Further, in the above-mentioned polymerization, the rate of polymerization and the molecular weight can also be adjusted by adding any of the known chain transfer agents and/or radical scavengers according to need.

The fluoropolymer is the one obtained by polymerizing a fluorine-containing monomer or monomers and, in accordance with the intended purpose, a fluorine-free monomer or monomers may be copolymerized.

As the fluorine-containing monomers, there may be mentioned, among others, fluoroolefins, preferably fluoroolefins containing 2 to 10 carbon atoms; fluorinated cyclic monomers; and fluorinated alkyl vinyl ethers represented by the formula $CY^2_2=CY^2OR^4$ or $CY^2_2=CYOR^5OR^6$ (in which $Y^2$ is H or F, $R^4$ and $R^6$ each is an alkyl group containing 1 to 8 carbon atoms as resulting from substitution of a part or the whole of the hydrogen atoms by a fluorine atom or atoms and $R^5$ is an alkylene group containing 1 to 8 carbon atoms as resulting from substitution of a part or the whole of the hydrogen atoms by a fluorine atom or atoms).

The fluoroolefins preferably contain 2 to 6 carbon atoms. As the fluoroolefins containing 2 to 6 carbon atoms, there may be mentioned, for example, tetrafluoroethylene [TFE], hexafluoropropylene [HFP], chlorotrifluoroethylene [CTFE], vinyl fluoride, vinylidene fluoride [VDF], trifluoroethylene, hexafluoroisobutylene and perfluorobutylethylene. As the fluorinated cyclic monomers, there may preferably be mentioned perfluoro-2,2-dimethyl-1,3-dioxole [PDD], perfluoro-2-methylene-4-methyl-1,3-dioxolane [PMD], etc.

Referring to the fluorinated alkyl vinyl ethers, each of $R^4$ and $R^6$ preferably contains 1 to 4 carbon atoms and, more preferably, is the one resulting from substitution of all the hydrogen atoms by fluorine atoms, while $R^5$ preferably contains 2 to 4 carbon atoms and, more preferably, is the one resulting from substitution of all the hydrogen atoms by fluorine atoms.

As the fluorine-free monomers, there may be mentioned hydrocarbon-derived monomers reactive with the fluorine-containing monomers. As the hydrocarbon-derived monomers, there may be mentioned, among others, alkenes such as ethylene, propylene, butylene and isobutylene; alkyl vinyl ethers such as ethyl vinyl ether, propyl vinyl ether, butyl vinyl ether, isobutyl vinyl ether and cyclohexyl vinyl ether; vinyl esters such as vinyl acetate, vinyl propionate, vinyl n-butyrate, vinyl isobutyrate, vinyl valerate, vinyl pivalate, vinyl caproate, vinyl caprylate, vinyl caprate, vinyl versatate, vinyl laurate, vinyl myristate, vinyl palmitate, vinyl stearate, vinyl benzoate, vinyl p-tert-butylbenzoate, vinyl cyclohexanecarboxylate, vinyl monochloroacetate, vinyl adipate, vinyl acrylate, vinyl methacrylate, vinyl crotonate, vinyl sorbate, vinyl cinnamate, vinyl undecylenate, vinyl hydroxyacetate, vinyl hydroxypropionate, vinyl hydroxybutyrate, vinyl hydroxyvalerate, vinyl hydroxyisobutyrate and vinyl hydroxycyclohexanecarboxylate; alkyl allyl ethers such as ethyl allyl ether, propyl allyl ether, butyl allyl ether, isobutyl allyl ether and cyclohexyl allyl ether; and alkyl allyl esters such as allyl acetate, allyl propionate, allyl butyrate, allyl isobutyrate and allyl cyclohexanecarboxylate.

The fluorine-free monomers may also include functional group-containing hydrocarbon-derived monomers. As the functional group-containing hydrocarbon-derived monomers, there may be mentioned, for example, hydroxyalkyl vinyl ethers such as hydroxyethyl vinyl ether, hydroxypropyl vinyl ether, hydroxybutyl vinyl ether, hydroxyisobutyl vinyl ether and hydroxycyclohexyl vinyl ether; carboxyl group-containing, fluorine-free monomers such as itaconic acid, succinic acid, succinic anhydride, fumaric acid, fumaric anhydride, crotonic acid, maleic acid, maleic anhydride and perfluorobutenoic acid; glycidyl group-containing, fluorine-free monomers such as glycidyl vinyl ether and glycidyl allyl ether; amino group-containing, fluorine-free monomers such as aminoalkyl vinyl ethers and aminoalkyl allyl ethers; and amide group-containing, fluorine-free monomers such as (meth)acrylamide and methylolacrylamide.

As the fluoropolymers suitably producible by the method of producing a fluoropolymer according to the invention, there may be mentioned TFE polymers in which the monomer showing the highest mole fraction (hereinafter, "most abundant monomer") among the monomers constituting the polymer is TFE, VDF polymers in which the most abundant monomer is VDF, CTFE polymers in which the most abundant monomer is CTFE, and so forth.

The TFE polymers may suitably be TFE homopolymers or copolymers derived from (1) TFE, (2) one or more fluorine-containing monomers other than TFE containing 2 to 8 carbon atoms, in particular HFP and/or CTFE, and (3) some other monomer or monomers. As the other monomers (3), there may be mentioned, for example, fluoro(alkyl vinyl ether) species containing 1 to 5 carbon atoms, in particular 1 to 3 carbon atoms; fluorodioxoles; perfluoroalkylethylenes; and ω-hydroperfluoroolefins.

The TFE polymers may further be copolymers of TFE and one or more fluorine-free monomers. As the fluorine-free monomers, there may be mentioned, for example, alkenes such as ethylene and propylene; vinyl esters; and vinyl ethers. The TFE polymers may further be copolymers derived from TFE, one or more fluorine-containing monomers containing 2 to 8 carbon atoms and one or more fluorine-free monomers.

The VDF polymers may suitably be VDF homopolymers [PVDF] or copolymers derived from (1) VDF, (2) one or more fluoroolefins other than VDF containing 2 to 8 carbon atoms, in particular TFE, HFP and/or CTFE, and (3) a perfluoro (alkyl vinyl ether) containing an alkyl group containing 1 to 5 carbon atoms, in particular 1 to 3 carbon atoms, among others.

The CTFE polymers may suitably be CTFE homopolymers or copolymers derived from (1) CTFE, (2) one or more fluoroolefins other than CTFE containing 2 to 8 carbon atoms, in particular TFE and/or HFP, and (3) a perfluoro(alkyl vinyl ether) containing an alkyl group containing 1 to 5 carbon atoms, in particular 1 to 3 carbon atoms.

The CTFE polymers may also be copolymers derived from CTFE and one or more fluorine-free monomers. Included among the fluorine-free monomers are alkenes such as ethylene and propylene; vinyl esters; and vinyl ethers.

The above-mentioned fluoropolymers produced by the method of producing a fluoropolymer according to the invention may be glass-like, plastic or elastomeric. These are non-crystalline or partially crystalline and can be subjected to compression baking processing, melt processing or non-melt processing.

The method of producing a fluoropolymer according to the invention can suitably be applied to the production of, for example, polytetrafluoroethylene polymers [PTFE polymers] as non-melt processible resins (I), ethylene/TFE copolymers [ETFEs], TFE/HFP copolymers [FEPs] and TFE/perfluoro (alkyl vinyl ether) copolymers [PFAs, MFAs, etc.] as melt processible polymers (II) and, as elastomeric copolymers (III), TFE/propylene copolymers, TFE/propylene/third monomer copolymers (the third monomer being VDF, HFP, CTFE, a perfluoro(alkyl vinyl ether) or the like), TFE/perfluoro(alkyl vinyl ether) copolymers; HFP/ethylene copolymers, HFP/ethylene/TFE copolymers; PVDF; VDF/HFP copolymers, HFP/ethylene copolymers, VDF/TFE/HFP copolymers and like thermoplastic elastomers; and fluorine-containing segmented polymers described in Japanese Patent Publication (Kokoku) S61-49327.

The above-mentioned perfluoro(alkyl vinyl ether) is represented by the formula:

$$OCF=CF_2$$

wherein $Rf^6$ represents a perfluoroalkyl group containing 1 to 6 carbon atoms, k3, k4 and k5 are the same or different and each is an integer of 0 to 5, and $Q^5$, $Q^6$ and $R^7$ are the same or different and each is F or $CF_3$.

The method of producing a fluoropolymer according to the invention is to produce a fluoropolymer.

By carrying out the above polymerization, the fluoropolymers are generally obtained in the form of aqueous dispersions with a concentration of 10 to 50% by mass. A preferred lower limit to the fluoropolymer concentration in the aqueous dispersions is 10% by mass, a more preferred lower limit is 15% by mass, a preferred upper limit is 40% by mass, a more preferred upper limit is 35% by mass and a still more preferred upper limit is 30% by mass.

The aqueous dispersions obtained by carrying out the above polymerization each may be subjected to concentration or dispersion stabilization treatment to give a dispersion, or to coagulation/flocculation or aggregation, which is followed by polymer recovery and drying to give a powder or some other solid matter. While the method of producing a fluoropolymer according to the invention is to produce a fluoropolymer, the fluoropolymer produced may be a fluoropolymer dispersed in the above-mentioned aqueous dispersions or fluoropolymer dispersed in such dispersions as mentioned above or fluoropolymer occurring as powder or other solid matter.

The above-mentioned non-melt processable resins (I), melt processable resins (II) and elastomeric polymers (III) suitably producible by the method of producing a fluoropolymer according to the invention are preferably produced in the following manner.

(I) Non-Melt Processable Resins

In the method of producing a fluoropolymer according to the invention, the polymerization of the PTFE polymers is generally carried out at a polymerization temperature of 10 to 100° C. and a polymerization pressure of 0.05 to 5 MPaG.

For the above polymerization, a pressure-resistant reaction vessel equipped with a stirrer is charged with pure water and one or more of the carboxylate ester bond-containing carboxylic acid derivatives and, after deoxygenation, charged with TFE and then heated to a predetermined temperature, and a polymerization initiator is added to initiate the reaction. Since otherwise the pressure lowers with the progress of the reaction, an additional amount of TFE is fed to the reaction vessel either continuously or intermittently so as to maintain the initial pressure. After feeding of the predetermined amount of TFE, the feeding is stopped, the TFE remaining in the reaction vessel is purged therefrom, and the temperature is returned to room temperature for termination of the reaction.

In producing the PTFE polymers, one or more of various known modifying monomers can also be used in combination. The polytetrafluoroethylene polymers [PTFE polymers] so referred to herein conceptually includes not only TFE homopolymers but also those copolymers of TFE and a modifying monomer or monomers which are non-melt processable (hereinafter such copolymers are referred to as "modified PTFEs").

As the modifying monomers, there may be mentioned, for example, perhaloolefins such as HFP and CTFE; fluoro(alkyl vinyl ether) species whose alkyl group contains 1 to 5 carbon atoms, in particular 1 to 3 carbon atoms; fluorinated cyclic monomers such as fluorodioxoles; perhaloalkylethylenes; and ω-hydroperhaloolefins. The modifying monomer(s) can be fed all at once initially, or continuously, or intermittently in divided portions according to the intended purpose and/or the feeding of TFE.

The modifying monomer content in the modified PTFEs is generally within the range of 0.001 to 2 mole percent.

In producing the PTFE polymers, the carboxylate ester bond-containing carboxylic acid derivatives can be used in the range mentioned above referring to the method of producing a fluoropolymer according to the invention. Generally, the level of addition thereof is 0.0001 to 5% by mass relative to the aqueous medium. If it is within the above range, the carboxylate ester bond-containing carboxylic acid derivative concentration is not particularly restricted but, generally, the addition level at the start of polymerization is not higher than the critical micelle concentration (CMC). At excessive addition levels, acicular particles with a high aspect ratio tend to form, giving gel-like aqueous dispersions with impaired stability.

In producing the PTFE polymers, a persulfate (e.g. ammonium persulfate) or an organic peroxide such as disuccinoyl peroxide or diglutaroyl peroxide can be used as the polymerization initiator either singly or in the form of a mixture of these. Redox systems resulting from combined use of a reducing agent such as sodium sulfite may also be used. Further, it is also possible to adjust the radical concentration in the polymerization system during polymerization by adding a radical scavenger such as hydroquinone or catechol or by adding a peroxide decomposer such as ammonium sulfite.

Usable as the chain transfer agent in producing the PTFE polymers are those known in the art, such as saturated hydrocarbons such as methane, ethane, propane and butane, halogenated hydrocarbons such as chloromethane, dichloromethane and difluoroethane, alcohols such as methanol and ethanol, and hydrogen. Those which are gaseous at ordinary temperature and ordinary pressure are preferred, however.

The usage of the chain transfer agent is generally 1 to 1000 ppm, preferably 1 to 500 ppm, relative to the total amount of TFE as fed.

In producing the PTFE polymers, a saturated hydrocarbon containing at least 12 carbon atoms which is substantially inert to the reaction and occurs as a liquid under the reaction conditions mentioned above can be further used as a dispersion stabilizer in the reaction system in an amount of 2 to 10 parts by mass per 100 parts by mass of the aqueous medium. Ammonium carbonate, ammonium phosphate or the like may also be added as a buffering agent for adjusting the pH during reaction.

At the time of completion of the polymerization of the PTFE polymers, aqueous dispersions having a solid matter concentration of 10 to 50% by mass and comprising PTFE polymer particles having an average particle diameter of 0.05 to 5000 μm or, in particular when one or more of the carboxylate ester bond-containing carboxylic acid derivatives are used, comprising very small PTFE polymer particles not larger than 0.3 μm in diameter can be obtained. The PTFE polymers at the time of completion of the polymerization have a number average molecular weight of 1,000 to 10,000,000.

The above aqueous PTFE polymer dispersions can be used in various fields of application in the form of fine powders after coagulation/flocculation and drying.

When such an aqueous PTFE polymer dispersion as mentioned above is subjected to coagulation/flocculation, the aqueous dispersion obtained by emulsion polymerization, in the form of a polymer latex, for instance, is generally diluted with water to a polymer concentration of 10 to 20% by mass, the pH is adjusted to neutral or alkaline according to circumstances, and the diluted dispersion is stirred in a vessel equipped with a stirrer more vigorously than the stirring during reaction. In the above coagulation/flocculation procedure, it is also possible to carry out the stirring while adding, as a coagulant/flocculant, a water-soluble organic compound such as methanol or acetone, an inorganic salt such as potassium nitrate or ammonium carbonate, or an inorganic acid such as hydrochloric acid, sulfuric acid or nitric acid, for instance. The coagulation/flocculation may also be carried out continuously using an in-line mixer or the like.

When a pigment(s) for coloration and/or one or more of various fillers for improving the mechanical properties are added prior to or during the coagulation/flocculation, pigmented and/or filled PTFE polymer-based fine powders with the pigment(s) and/or filler(s) uniformly distributed therein can be obtained.

The drying of the wet powders obtained by coagulation/flocculation of the above-mentioned aqueous PTFE polymer dispersions is generally carried out using such means as vacuum, high frequency heating or hot air while maintaining the powders in a condition hardly allowing the wet powders to flow freely, preferably in a stationary condition. Generally, friction among powder particles, especially at high temperatures, adversely affects the fine powder type PTFE polymers. This is because of the structures of PTFE polymer particles of this kind such that they readily fibrillate upon exposure to a weak shearing force and lose their original stable particle structure.

The above-mentioned drying is carried out at a drying temperature of 10 to 250° C., preferably 100 to 200° C.

In the after-treatment carried out after the above-mentioned polymerization, the carboxylate ester bond-containing carboxylic acid derivatives are generally hydrolyzed to give hydrolyzates.

The PTFE polymer-based fine powders obtained are preferably used for molding purposes, and suitable fields of application thereof includes hydraulic system and fuel system tubes and so forth for use in aircrafts and automobiles, flexible hoses for transporting liquid chemicals, steam and so forth, and electric wire coverings.

The aqueous PTFE polymer dispersions obtained by the above polymerization are also preferably used in various fields of application in the form of compositions prepared by adding a nonionic surfactant for stabilization and further concentration of the resulting dispersions and adding an organic and/or inorganic filler(s) thereto. When applied onto metal or ceramic substrates, the compositions can give coat layer surfaces having nonstickiness and a low coefficient of friction and excellent in gloss, smoothness, wear resistance, weather resistance and heat resistance. Thus, they are suited for use in coating rolls, cooking utensils and in impregnating glass cloths, for instance.

(II) Melt Processible Resins (1) In the method of producing a fluoropolymer of the invention, preferably, the polymerization for producing FEPs is carried out generally at a polymerization temperature of 60 to 100° C. and a polymerization pressure of 0.7 to 4.5 MPaG.

The FEPs preferably have a monomer composition (in % by mass) of TFE:HFP=(60 to 95):(5 to 40), more preferably (85 to 90):(10 to 15). The FEPs may also be modifications obtained by further using a perfluoro(alkyl vinyl ether) species as a third component in an amount within the range of 0.5 to 2% by mass of all the monomers.

In producing such FEPs as mentioned above by polymerization, the carboxylate ester bond-containing carboxylic acid derivatives can be used within the usage range mentioned above for the method of producing fluoropolymers according to the invention. Generally, however, they are used at an addition level of 0.0001 to 5% by mass relative to the aqueous medium.

Preferred for use as the chain transfer agent in producing the FEP by polymerization are cyclohexane, methanol, ethanol, carbon tetrachloride, chloroform, methylene chloride and methyl chloride, among others. As for the pH buffering agent, ammonium carbonate and disodium hydrogen phosphate, among others, are preferably used.

(2) In the method of producing a fluoropolymer of the invention, preferably, the polymerization for producing TFE/perfluoro(alkyl vinyl ether) copolymers such as PFA or MFA copolymers is generally carried out at a polymerization temperature of 60 to 100° C. and a polymerization pressure of 0.7 to 2.5 MPaG.

The TFE/perfluoro(alkyl vinyl ether) copolymers preferably have a monomer composition (in mole percent) of TFE:perfluoro(alkyl vinyl ether)=(95 to 99.7):(0.3 to 5), more preferably (98 to 99.5):(0.5 to 2). Preferably used as the perfluoro(alkyl vinyl ether) are those represented by the formula: $CF_2$=CFORf (in which Rf is a perfluoroalkyl group containing 1 to 6 carbon atoms).

In producing the above TFE/perfluoro(alkyl vinyl ether) copolymers by polymerization, the above-mentioned carboxylate ester bond-containing carboxylic acid derivatives can be used within the usage range mentioned above for the method of producing fluoropolymers according to the invention. Generally, however, they are used at an addition level of 0.0001 to 2% by mass relative to the aqueous medium.

Preferably used as the chain transfer agent in producing the TFE/perfluoro(alkyl vinyl ether) copolymers by polymerization are cyclohexane, methanol, ethanol, carbon tetrachloride, chloroform, methylene chloride, methyl chloride, methane and ethane, among others. As for the pH buffering agent, ammonium carbonate and disodium hydrogen phosphate, among others, are preferably used.

(3) In the method of producing a fluoropolymer of the invention, preferably, the polymerization for producing ETFE copolymers is generally carried out at a polymerization temperature of 20 to 100° C. and a polymerization pressure of 0.5 to 0.8 MPaG.

The ETFEs preferably have a monomer composition (in mole percent) of TFE:ethylene=(50 to 99):(50 to 1). The ETFEs may also be modifications obtained by further using a third monomer in an amount within the range of 0 to 20% by mass of all the monomers. The monomer composition is preferably TFE:ethylene:third monomer=(70 to 98):(30 to 2):(4 to 10). Preferred as the third monomer are perfluorobutylethylene, perfluorobutylethylene, 2,3,3,4,4,5,5-heptafluoro-1-pentene ($CH_2$=$CFCF_2CF_2CF_2H$) and 2-trifluoromethyl-3,3,3-trifluoropropene (($CF_3$)$_2$C=$CH_2$).

In producing the above ETFEs by polymerization, the above-mentioned carboxylate ester bond-containing carboxylic acid derivatives can be used within the usage range mentioned above for the method of producing a fluoropolymer according to the invention. Generally, however, they are used at an addition level of 0.0001 to 2% by mass relative to the aqueous medium.

Preferably used as the chain transfer agent in producing the ETFEs by polymerization are cyclohexane, methanol, ethanol, carbon tetrachloride, chloroform, methylene chloride and methyl chloride, among others.

(III) Elastomeric Polymers

For the polymerization for producing elastomeric polymers by the method of producing a fluoropolymer according to the invention, a pressure-resistant reaction vessel equipped with a stirrer is charged with pure water and one or more of the carboxylate ester bond-containing carboxylic acid derivatives and, after deoxygenation, charged with the monomers and then heated to a predetermined temperature, and a polymerization initiator is added to initiate the reaction. Since otherwise the pressure lowers with the progress of the reaction, additional amounts of the monomers are fed to the reaction vessel either continuously or intermittently so as to maintain the initial pressure. After feeding of the predetermined amounts of the monomers, the feeding is stopped, the monomers remaining in the reaction vessel are purged therefrom, and the temperature is returned to room temperature for termination of the reaction. In the case of emulsion polymerization, the polymer latex is preferably taken out of the reaction vessel continuously.

In particular when a thermoplastic elastomer is to be produced, it is possible to employ a method by which the final-stage rate of polymerization can be increased as compared with the ordinary polymerization techniques which method comprises once synthesizing fine fluoropolymer particles at a high carboxylate ester bond-containing carboxylic acid concentration, then diluting the system and further carrying out the polymerization, as disclosed in WO 00/01741.

The polymerization for producing the elastomeric polymers is carried out generally at a polymerization temperature of −20 to 200° C., preferably 5 to 150° C., and generally at a polymerization pressure of 0.5 to 10 MPaG, preferably 1 to 7 MPaG, although the conditions are to be appropriately selected from the viewpoint of the desired physical properties of the polymers and of controlling the rate of polymerization. The pH of the polymerization medium is preferably maintained generally at 2.5 to 9 in the conventional manner using such a pH adjusting agent as described later herein.

As the monomers for use in the polymerization for producing the elastomeric polymers, there may be mentioned, in addition to vinylidene fluoride, fluorine-containing, ethylenically unsaturated monomers containing at least the same number of fluorine atoms as the number of carbon atoms and capable of copolymerizing with vinylidene fluoride. As the fluorine-containing, ethylenically unsaturated monomers, there may be mentioned trifluoropropene, pentafluoropropene, hexafluorobutene and octafluorobutene. Among them, hexafluoropropene is particularly suited for use in view of the elastomer characteristics obtainable when it intercepts the polymer crystal growth. As the fluorine-containing, ethylenically unsaturated monomers, there may also be mentioned trifluoroethylene, TFE, CTFE, etc. Fluorine-containing monomers containing one or more chlorine- and/or bromine-substituted groups may also be used. Perfluoro(alkyl vinyl ether) species, for example perfluoro(methyl vinyl ether), can also be used. TFE and HFP are preferred in producing the elastomeric polymers.

The elastomeric polymers preferably have a monomer composition (in % by mass) of vinylidene fluoride:HFP:TFE (20 to 70):(20 to 60):(0 to 40). The elastomeric polymers having such a composition show good elastomer characteristics, chemical resistance and heat stability.

In producing the elastomeric polymers by polymerization, the above-mentioned carboxylate ester bond-containing carboxylic acid derivatives can be used within the usage range mentioned above for the method of producing fluoropolymers according to the invention. Generally, however, they are used at an addition level of 0.0001 to 5% by mass relative to the aqueous medium.

In producing the elastomeric polymers by polymerization, an inorganic radical polymerization initiator known in the art can be used as a polymerization initiator. Particularly useful as the inorganic radical polymerization initiator are those water-soluble inorganic peroxides known in the art, for example sodium, potassium and ammonium persulfates, perphosphates, perborates, percarbonates or permanganates. Those radical polymerization initiators can be further activated by a reducing agent, for example sodium, potassium or ammonium sulfite, bisulfite, metabisulfite, hyposulfite, thiosulfate, phosphite or hypophosphite, or by a readily oxidizable metal compound, for example a ferrous salt, a cuprous salt or a silver salt. Ammonium persulfate is preferred as the inorganic radical polymerization initiator, and the use of ammonium persulfate together with sodium bisulfite in a redox system is more preferred.

The level of addition of the above polymerization initiator is appropriately selected within the range of 0.0001 to 10% by mass, preferably 0.01 to 5% by mass, relative to all the monomers according to the desired polymer molecular weight and the rate of the polymerization reaction.

In producing the elastomeric polymers by polymerization, those chain transfer agents known in the art can be used. In the case of PVDF polymerization, hydrocarbons, esters, ethers, alcohols, ketones, chlorine compounds and carbonates, among others, can be used and, in the case of thermoplastic elastomers, hydrocarbons, esters, ethers, alcohols, chlorine compounds and iodine compounds, among others, can be used. Among them, acetone and isopropyl alcohol are preferred in PVDF polymerization and, in the case of thermoplastic elastomer polymerization, isopentane, diethyl malonate and ethyl acetate are preferred from the viewpoint of their hardly causing reductions in rate of reaction, and diiodo compounds such as $I(CF_2)_4I$, $I(CF_2)_6I$ and $ICH_2I$ are preferred from the viewpoint of their being capable of iodinating polymer termini to give reactive polymers.

The chain transfer agent is generally used in an amount of $0.5 \times 10^{-3}$ to $5 \times 10^{-3}$ mole percent, preferably $1.0 \times 10^{-3}$ to $3.5 \times 10^{-3}$ mole percent, relative to all the monomers to be fed.

In the elastomeric polymer polymerization, paraffin wax or the like can be preferably used as an emulsion stabilizer in the case of PVDF polymerization and, in the case of thermoplastic elastomer polymerization, a phosphate salt, sodium hydroxide or potassium hydroxide, for instance, can be preferably used as a pH adjusting agent.

The elastomeric polymers obtained by the method of producing a fluoropolymer according to the invention have, at the time of completion of the polymerization, a solid matter concentration of 10 to 40% by mass, an average particle diameter of 0.03 to 1 μm, preferably 0.05 to 0.5 μm, and a number average molecular weight of 1,000 to 2,000,000.

The elastomeric polymer obtained by the method of producing a fluoropolymer according to the invention can be made into dispersions suited for rubber molding processing by adding a dispersion stabilizer such as a hydrocarbon-derived surfactant and/or concentration and/or other processing according to need. The dispersions are subjected to such treatments as pH adjustment, coagulation/flocculation and heating. Each treatment is carried out in the following manner.

The pH adjustment consists in adding a mineral acid such as nitric acid, sulfuric acid, hydrochloric acid or phosphoric acid and/or a carboxylic acid containing not more than 5 carbon atoms and having a $pK \leq 4.2$ to thereby lower the pH to 2 or below.

The coagulation/flocculation is carried out by adding an alkaline earth metal salt. As the alkaline earth metal salt, there may be mentioned calcium or magnesium nitrate, chlorate and acetate.

Although either of the pH adjustment and coagulation/flocculation may be carried out first, the pH adjustment is preferably carried out first.

After each procedure, each elastomer is washed with the equal volume of water to remove small amounts of the buffer and/or the salt and other impurities occurring in the elastomer, and then dried. The drying is generally carried out in a drying oven at an elevated temperature of about 70 to 200° C. while circulation air through the oven.

In each of the above treatments, the carboxylate ester bond-containing carboxylic acid derivatives are generally hydrolyzed and form hydrolyzates.

The carboxylate ester bond-containing carboxylic acid derivatives can also be suitably used as dispersants for dispersing the fluoropolymers obtained by polymerization in aqueous media.

The fluoropolymer aqueous dispersion of the invention is a fluoropolymer aqueous dispersion comprising a particle comprising a fluoropolymer, a carboxylate ester bond-containing carboxylic acid derivative and an aqueous medium.

The fluoropolymer aqueous dispersion of the invention is a dispersion wherein the particle comprising a fluoropolymer is dispersed in an aqueous medium in the presence of the above carboxylate ester bond-containing carboxylic acid derivative.

In the fluoropolymer aqueous dispersion of the invention, the above carboxylate ester bond-containing carboxylic acid derivative is the same as the carboxylate ester bond-containing carboxylic acid derivative mentioned hereinabove referring to the method of producing a fluoropolymer according to the invention. The carboxylate ester bond-containing carboxylic acid derivatives is preferably the one capable of forming a hydrolyzate upon hydrolysis.

The hydrolyzates are generally volatile and can be eliminated by heating. As the hydrolyzates, there may be mentioned, for example, those given hereinabove as examples referring to the method of producing a fluoropolymer according to the invention. The heating includes, among others, heating and/or baking following application of a coating composition prepared from the fluoropolymer aqueous dispersion of the invention to substrates, drying and/or pelletization of the wet powder obtained by coagulation/flocculation of the fluoropolymer aqueous dispersion, and heating in molding or other processing using the dry powder or pellets obtained. The heating is preferably carried out at a temperature of about 10 to 250° C.

Preferred as the carboxylate ester bond-containing carboxylic acid derivatives to be used in the fluoropolymer aqueous dispersion of the invention are the 2-acyloxycarboxylic acid derivatives represented by the general formula (1) given hereinabove and the dicarboxylic acid half esters represented by the general formula (2) given hereinabove, among others, in view of their good dispersing power and their ready eliminability from the powders, pellets, moldings, coatings and so forth obtained from the fluoropolymer aqueous dispersion.

The carboxylate ester bond-containing carboxylic acid derivatives preferably amount to 0.0001 to 15% by mass of the fluoropolymer aqueous dispersion of the invention. At levels below 0.0001% by mass, the dispersion stability may be poor in certain cases, while levels exceeding 15% by mass will produce no further dispersing effect proportional to their abundance, hence are impractical. A more preferred lower limit to the content of the carboxylate ester bond-containing carboxylic acid derivatives is 0.001% by mass, and a more preferred upper limit thereto is 10% by mass and a still more preferred upper limit is 2% by mass.

The fluoropolymer aqueous dispersion of the invention may be an aqueous dispersion obtained by carrying out the polymerization mentioned above, a dispersion obtained by subjecting that aqueous dispersion to concentration or dispersion stabilization treatment, or one obtained by dispersing a fluoropolymer powder in an aqueous medium in the presence of at least one of the carboxylate ester bond-containing carboxylic acids mentioned above.

As for the method of concentration, any of the methods known in the art can be employed, and the fluoropolymer concentration can be increased to 40 to 60% by mass according to the intended use. The stability of the dispersion may be impaired upon concentration but, in such a case, a dispersion stabilizer may be further added. Any of the above-mentioned carboxylate ester bond-containing carboxylic acid derivatives or any of various surfactants may be added as the dispersion stabilizer. The various dispersion stabilizers include, but are not limited to, nonionic surfactants such as polyoxyalkyl ethers, in particular polyoxyethylene alkylphenyl ethers (e.g. Triton X-100 (trademark), product of Rohm & Haas), polyoxyethylene isotridecyl ether (Dispanol TOC (trademark), product of NOF (Nippon Oil and Fat) Corporation), polyoxyethylenepropyl tridecyl ether and other polyoxyethylene ethers.

The total amount of the dispersion stabilizers corresponds to a concentration of 0.5 to 20% by mass relative to the solid matter of the dispersion. At levels below 0.5% by mass, the dispersion stability may be poor in certain cases, while levels exceeding 20% by mass will produce no further dispersing effect proportional to their abundance, hence are impractical. A more preferred lower limit to the dispersion stabilizer content is 2% by mass, and a more preferred upper limit is 12% by mass.

The aqueous dispersion obtained by carrying out the polymerization mentioned above, without concentration, can be subjected to dispersion stabilization treatment according to the intended use thereof so that a fluoropolymer aqueous dispersion with a long pot life may be prepared. As the dispersion stabilizer to be used, there may be mentioned the same ones as those mentioned hereinabove.

The fields of application of the fluoropolymer aqueous dispersion of the invention are not particularly restricted but include, among others, the application of the aqueous dispersion as such in forming coatings by application thereof to substrates followed by drying, if necessary further followed by baking; in impregnating porous supports such as nonwoven fabrics and resin moldings therewith, followed by drying, preferably further followed by baking; and in cast film formation by application onto a glass or like substrate, drying, if necessary immersing in water, and peeling off the resulting thin film from the substrate. As examples of such applications, there may be mentioned aqueous dispersion type coating compositions, electrode binders, and water repellents for electrodes, among others.

The fluoropolymer aqueous dispersion of the invention can be used as a water-thinned coating composition after incorporation therein of one or more of the pigments, thickening agents, dispersants, antifoaming agents, antifreezing agents, film forming auxiliaries and other ingredients, which are known in the art, and/or after further addition thereto of some other high-molecular compound.

As a field of application of the fluoropolymer aqueous dispersion of the invention, there may further be mentioned the use of a powder obtained by subjecting the fluoropolymer aqueous dispersion to coagulation or aggregation, recovering the solid matter and drying the same, if desired followed by granulation. The coagulation or aggregation can be carried out employing any of the conventional methods known in the art as they are.

The above-mentioned 2-acyloxycarboxylic acid derivatives represented by the general formula (1):

wherein $Rf^1$ and $Rf^2$ are the same or different and each represents H, F, a fluoroalkyl group containing 1 to 20 carbon atoms or an ether oxygen-containing fluoroalkyl group containing 1 to 20 carbon atoms, a and b each represents an integer of 0 to 2, d represents an integer of 1 to 3, provided that a, b and d satisfy the relation a+b+d=3; Rf and M are as defined above; $Rf^1$, $Rf^2$ and Rf are the same or different, also constitute an aspect of the present invention.

The 2-acyloxycarboxylic acid derivatives of the invention can show surfactant activity and are suited for use as emulsifiers to be present in an aqueous medium on the occasion of producing fluoropolymers by carrying out the polymerization in the aqueous medium and, further, as dispersants in fluoropolymer aqueous dispersions comprising fluoropolymer particles dispersed in an aqueous medium. After the use as such emulsifiers or dispersants as mentioned above, the 2-acyloxycarboxylic acid derivatives of the invention can be recovered and used repeatedly.

The 2-acyloxycarboxylic acid derivatives of the invention, when subjected to after-treatment, for example coagulation/flocculation, following the above-mentioned polymerization, readily undergo hydrolysis of the ester moiety, and the resulting hydrolyzates are generally volatile and can be eliminated by heating. The heating includes, among others, heating and/or baking following application of a coating composition prepared from the above-mentioned fluoropolymer aqueous dispersion to substrates, drying and/or pelletization of the wet powder obtained by coagulation/flocculation of the fluoropolymer aqueous dispersion, and heating in molding or other processing using the dry powder or pellets obtained.

The 2-acyloxycarboxylic acid derivatives of the invention can thus exhibit surfactant activity as emulsifiers on the occasion of producing fluoropolymers by polymerization or as dispersants or like agents in fluoropolymer aqueous dispersions and, at the same time, can be hydrolyzed and eliminated with ease by after-treatment and, since they do not remain in the fluoropolymer-based powders, pellets, moldings, coatings and others obtained, it becomes possible to prevent foaming during processing, improve the physical properties and prevent discoloration of such moldings, coatings and so forth.

The substituents, number of carbon atoms and compounds preferred in or as the 2-acyloxycarboxylic acid derivatives of the invention are the same as those mentioned hereinabove referring to the method of producing a fluoropolymer according to the invention.

The method of producing the 2-acyloxycarboxylic acid derivatives of the invention is not particularly restricted but, for example, the method comprising esterifying a 2-hydroxycarboxylic acid derivative represented by the general formula (5):

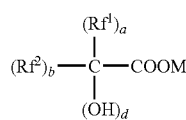

(5)

wherein $Rf^1$, $Rf^2$, M, a, b and d are as defined above, to introduce RfCO— ($Rf^3$ being as defined above) into the 2-hydroxyl group is preferred.

Preferred as the above 2-hydroxycarboxylic acid derivative are, for example, $(CF_3)_2C(OH)COOM$, $(CF_3)(CF_3CF_2)C$(OH)COOM, $(CF_3CF_2)_2C(OH)COOM$, $(CF_3)C(OH)_2$COOM, $(CF_3CF_2)C(OH)_2COOM$ and $(CF_3)C(OH)_2$ COOM (M being as defined above).

The 2-hydroxycarboxylic acid derivatives can be prepared, for example, by the methods described below.

(A) In the Case of d=1

The method comprising preparing a 2-hydroxycarboxylic acid ester from a fluoroalkenyl ether and further hydrolyzing this ester in the conventional manner to give the corresponding 2-hydroxycarboxylic acid or a salt thereof.

As the fluoroalkenyl ether, there may be mentioned, among others, heptafluoroisobutenyl alkyl ethers $[(CF_3)_2$C=CFOR$^1$ in which $R^1$ is an alkyl group containing 1 to 12 carbon atoms] obtainable, for example, by using octafluoroisobutene formed as a byproduct in the production of hexafluoropropene as a starting material and converting this to an alcohol adduct and then subjecting the adduct to dehydrofluorination.

As the method of preparing the 2-hydroxycarboxylic acid ester from the fluoroalkenyl ether, there may be mentioned the method based on the oxidation reaction using a ruthenium compound or an osmium compound.

As the oxidation reaction, there may be mentioned, among others, the oxidation methods described in Japanese Kokai Publication 2002-234860, for example the oxidation reaction using a stoichiometric amount of $RuO_4$, the catalytic oxidation comprising oxidizing such a precursor as $RuO_2.H_2O$ or $RuCl_3.nH_2O$ with a cooxidizing agent to give $RuO_4$ which contributes to the oxidation reaction, the oxidation reaction using a stoichiometric amount of $OsO_4$, and the catalytic oxidation comprising oxidizing an appropriate precursor with a cooxidizing agent to give $OsO_4$ which contributes to the oxidation reaction.

(B) In the Case of d=2

The method according to which a compound represented by the formula $CF_3(CF_2)_zCFCF_2O$ (in which z represents an integer of 1 to 17 and —$CFCF_2O$ represents an epoxy structure) is used as a starting material and a compound represented by the formula $CF_3(CF_2)_zC(OH)_2COOH$ (in which z is as defined above) is obtained by the method described in J. Org. Chem., 31, 2312 (1966).

The method of esterifying the above-mentioned 2-hydroxycarboxylic acid derivative is not particularly restricted but, for example, the following methods can be employed.

(I) The method comprising reacting with an acyl halide prepared from RfCOOH(Rf being as defined above) in the manner of dehydrohalogenation reaction.

(II) The method comprising reacting with a carboxylic acid represented by the formula RfCOOM$^1$ (in which Rf being as defined above and M$^1$ represents H, $NH_4$, Li, Na or K) or a salt thereof in the manner of dehydration reaction.

(III) The method comprising reacting with an acid ester represented by the formula RfCOOR$^2$ (in which Rf is as defined above and R$^2$ is an alkyl group containing 1 to 12 carbon atoms) in the manner of transesterification.

(IV) The method comprising reacting with an acid anhydride represented by the formula RfCOOCOR$^3$ (in which Rf is as defined above and R$^3$ represents Rf or an alkyl group containing 1 to 12 carbon atoms).

Among the above-mentioned methods (I)-(IV), the method (I) or (II) is preferably employed from the viewpoint of operability, yield, etc.

Referring to the method (I), the acyl halide may be RfCOF, RfCOCl, RfCOBr or RfCOI (Rf being as defined above). RfCOF and RfCOCl are preferred, however.

Preferred as the method of producing the 2-acyloxycarboxylic acids of the invention is the method comprising esterifying a 2-hydroxycarboxylic acid derivative represented by the general formula (2) given above with an alkanoyl compound represented by the general formula (6):

RfCOZ  (6)

wherein Rf is as defined above and Z represents —OM$^1$ (M$^1$ representing H, NH$_4$, Li, Na or K) or Y (Y representing F or Cl) to produce the corresponding 2-acyloxycarboxylic acid derivative. This method also constitutes an aspect of the present invention.

This method corresponds to the method (I) mentioned above in which the halogen in the acyl halide is F or Cl and to the method (II) mentioned above.

As a specific example of the method (I) mentioned above where Y is Cl, for instance, there may be mentioned the method comprising adding thionyl chloride dropwise to the above RfCOOH within the temperature range of 0 to 100° C. in the presence of an organic solvent such as benzene, toluene or chloroform to give the corresponding acid chloride [Rf-COCl] as the above-mentioned alkanoyl compound and then adding an amount within the range of 0.8 to 1.2 equivalents of the above acid chloride dropwise to the above-mentioned 2-hydroxycarboxylic acid derivative within the temperature range of 0 to 100° C. in the presence of an acid acceptor such as pyridine or triethylamine and of the above-mentioned organic solvent, followed by several hours of stirring.

The acid acceptor is preferably used within the usage range of 0.1 to 2 equivalents relative to the 2-hydroxycarboxylic acid derivative.

As an example of the method (II) mentioned above, there may be mentioned the method comprising reacting the 2-hydroxycarboxylic acid derivative with the above-mentioned RfCOOM$^1$ at 50 to 100° C. in the presence of an organic solvent such as hexane, cyclohexane, benzene, toluene or chloroform and of a dehydrating agent such as phosphorus pentoxide or sulfuric acid.

The dehydrating agent is preferably used in an amount of 0.7 to 5 equivalents relative to the 2-hydroxycarboxylic acid derivative, and the amount of the above-mentioned RfCOOM$^1$ to be added dropwise is preferably within the range of 0.7 to 2 equivalents relative to the 2-hydroxycarboxylic acid derivative.

The group R$^2$ in the above-mentioned RfCOOR$^2$ to be used in carrying out the method (III) mentioned above is, for example, methyl, ethyl or propyl and, among them, methyl is preferred.

The 2-acyloxycarboxylic acid derivatives of the invention can be suitably used as surfactants.

Such a surfactant comprising the 2-acyloxycarboxylic acid derivatives mentioned above also constitutes a further aspect of the present invention.

When it contains at least one of the 2-acyloxycarboxylic acid derivatives represented by the general formula (1) given hereinabove, the surfactant of the invention can serve as a surfactant satisfactorily. It may, however, contain two or more of the 2-acyloxycarboxylic acid derivatives.

The surfactant of the invention may contain, in addition to the above 2-acyloxycarboxylic acid derivative(s), one or more other compounds having surfactant activity.

The other compounds having surfactant activity are not particularly restricted but may be anionic, cationic, nonionic or betaine type surfactants, and these surfactants may be hydrocarbon-derived ones.

The surfactant of the invention may further contain, in addition to the 2-acyloxycarboxylic acid derivative(s) and the other compound(s) having surfactant activity as optionally employed, at least one additive. The additive is not particularly restricted but may be any one generally used in conventional surfactants, for example a stabilizer.

The surfactant of the invention, which comprises the above-mentioned 2-acyloxycarboxylic acid derivative(s), can exhibit an appropriate level of surfactant activity in various fields of application. When admixed with various liquids, typically water, the surfactant of the invention is effective in reducing the surface tension, and the addition level and the intended surface tension level can be properly selected according to the intended purpose.

Effects of the Invention

The method of producing a fluoropolymer according to the invention, which has the constitution described hereinabove, can efficiently produce the fluoropolymer having a very low residual surfactant content in the resins and having good physical properties with little discoloration. The fluoropolymer aqueous dispersion of the invention, which has the constitution described hereinabove, can allow the fluoropolymer to occur stably and can provide a fluoropolymer-based molding, a coating and so forth with good physical properties with little discoloration. The 2-acyloxycarboxylic acid derivative of the invention, which have the constitution described hereinabove, can be suitably used as a surfactant and so on. The surfactant of the invention comprises the 2-acyloxycarboxylic acid derivative(s) mentioned above and therefore has appropriate surfactant activity.

BEST MODES FOR CARRYING OUT THE INVENTION

In the following, the present invention is described in terms of certain production examples and working examples. Such production examples and working examples are, however, by no means limitative of the scope of the present invention.

Production Example 1

Synthesis of (CF$_3$)$_2$C(OCOCF$_2$CF$_2$CF$_2$H)COONH$_4$

[1] Synthesis of (CF$_3$)$_2$C(OH)COOCH$_3$

A 1000-mL three-necked round bottom flask equipped with a dropping funnel, condenser, thermometer and stirrer was charged with 53.0 g (0.25 mol) of (CF$_3$)$_2$C=CFOCH$_3$, 0.03 g (0.25 mmol) of RuO$_2$.nH$_2$O, 17.3 g (0.13 mol) of K$_2$CO$_3$ and 40.0 g of water and, with stirring at room temperature, the reaction was caused to proceed by dropwise addition of 1.7 mol/L sodium hypochlorite to generate RuO$_4$ from the RuO$_2$.nH$_2$O. At the time when the reaction time arrived at 6 hours, the amount of the 1.7 mol/L sodium hypochlorite charged was 147 g (0.25 mol). After return of the RuO$_4$ to RuO$_2$.nH$_2$O, the RuO$_2$.nH$_2$O was filtered off from the reaction mixture, and the filtrate obtained was allowed to separate into two phases in a separating funnel. Analysis of the thus-obtained organic layer by gas chromatography revealed that the degree of conversion of (CF$_3$)$_2$C=CFOCH$_3$ was 99.8% and (CF$_3$)$_2$C(OH)COOCH$_3$ was formed with a selectivity of 90.5%.

[2] Synthesis of (CF$_3$)$_2$C(OH)COOH

A 100-mL three-necked round bottom flask equipped with a condenser, thermometer and stirrer was charged with 0.9 g of sodium hydroxide and 20 mL of methanol, and uniform dissolution was effected by means of the stirrer. To this solution was added dropwise 4.5 g of (CF$_3$)$_2$C(OH)COOCH$_3$ over 3 minutes, followed by dropwise addition of 2 mL of water.

The resulting mixture was stirred at 20° C. for 1 hour. The methanol was then distilled off under reduced pressure, 10 mL of water added and then 35% hydrochloric acid was added until the pH became 2. Chloroform (20 mL) was added, and the oil layer was separated and recovered. The chloroform was distilled off, whereupon 3.9 g of $(CF_3)_2C(OH)COOH$ was obtained.

[3] Synthesis of $(CF_3)_2C(OCOCF_2CF_2CF_2CF_2H)COONH_4$

A 100-mL three-necked flask equipped with a condenser, thermometer and stirrer was charged with 2.1 g of $(CF_3)_2C(OH)COOH$ and 20 mL of chloroform and, with stirring at 20° C., 1.6 g of triethylamine was added dropwise over 5 minutes. After completion of the dropping, 4.1 g of $HCF_2CF_2CF_2CF_2COCl$ was added dropwise over 10 minutes. After an hour of stirring, 20 mL of water was added and, after stirring for washing, the oil layer was separated and the chloroform was distilled off to give 3.1 g of $(CF_3)_2C(OCOCF_2CF_2CF_2CF_2H)COOH$. Neutralization of this compound with aqueous ammonia gave

$CF_3)_2C(OCOCF_2CF_2CF_2CF_2H)COONH_4$.

Production Example 2

Synthesis of $(CF_3)_2C(OCOCF_2CF_2CF_2CF_2H)COOH$

A 100-mL three-necked flask equipped with a condenser, thermometer and stirrer was charged with 2.1 g of $(CF_3)_2C(OH)COOH$ and 20 mL of chloroform and, with stirring at 20° C., 1.6 g of triethylamine was added dropwise over 5 minutes. After completion of the dropping, 4.1 g of $HCF_2CF_2CF_2CF_2COCl$ was added dropwise over 10 minutes. After an hour of stirring, 20 mL of water was added and, after stirring for washing, the oil layer was separated and the chloroform was distilled off to give 3.1 g of $(CF_3)_2C(OCOCF_2CF_2CF_2CF_2H)COOH$. This compound was neutralized with aqueous ammonia.

A portion of the aqueous solution obtained was adjusted to a $(CF_3)_2C(OCOCF_2CF_2CF_2CF_2H)COOH$ concentration of 0.1% by mass, and the surface tension was measured at 25° C. by Wilhelmy method and found to be 62 Nm/m.

Production Example 3

Synthesis of $CF_3C(OCOCF_2CF_2CF_2CF_2H)_2COOH$

A 100-mL three-necked flask equipped with a condenser, thermometer and stirrer was charged with 1.0 g of $CF_3C(OH)_2COOH$ and 20 ml of chloroform and, with stirring at 20° C., 1.5 g of triethylamine was added dropwise over 5 minutes. After completion of the dropping, 3.4 g of $HCF_2CF_2CF_2CF_2COCl$ was added dropwise over 10 minutes. After an hour of stirring, 20 ml of water was added and, after stirring for washing, the oil layer was separated and the chloroform was distilled off to give 1.3 g of $CF_3C(OCOCF_2CF_2CF_2CF_2H)_2COOH$. This compound was neutralized with aqueous ammonia.

A portion of the aqueous solution obtained was adjusted to a $CF_3C(OCOCF_2CF_2CF_2CF_2H)_2COOH$ concentration of 0.1% by mass, and the surface tension was measured at 25° C. by Wilhelmy method and found to be 56 Nm/m.

Production Example 4

Synthesis of $HCF_2CF_2CF_2CF_2CH_2OOCCH=CH—COONH_4$

A 100-mL three-necked flask equipped with a condenser, thermometer and stirrer was charged with 5.0 g of maleic anhydride and 40.0 g of $HCF_2CF_2CF_2CF_2CH_2CH_2OH$, the mixture was warmed to 70° C., 0.3 ml of concentrated sulfuric acid was added, and the reaction was allowed to proceed at 70° C. for 3 hours. Water was added to the reaction mixture for washing, followed by phase separation. After three repetitions of this washing procedure, the oil layer was recovered and the residual alcohol was distilled off therefrom to give 13.7 g of $HCF_2CF_2CF_2CF_2CH_2OOCCH=CH—COOH$. This compound was neutralized with ammonia to give $HCF_2CF_2CF_2CF_2CH_2OOCCH=CH—COONH_4$.

Example 1

Preparation of a PTFE latex [1]

A 3-L stainless steel autoclave equipped with a stirring blade was charged with 1.5 L of deionized water, 60 g of paraffin wax (melting point 60° C.) and 250 mg of the 2-acyloxycarboxylic acid derivative $(CF_3)_2C(OCOCF_2CF_2CF_2CF_2H)COONH_4$, and the system inside was substituted by tetrafluoroethylene [TFE]. The inside temperature was raised to 70° C., TFE was fed to the autoclave under pressure until arrival of the internal pressure at 0.78 MPa, and 5 g of a 0.6% (by weight) aqueous solution of ammonium persulfate [APS] was added to initiate the reaction. Since the pressure within the polymerization system otherwise lowered with the progress of the reaction, TFE was additionally fed continuously to maintain the inside pressure at 0.78 MPa, and the reaction was continued. After feeding TFE until arrival of the resin solid content in the aqueous dispersion at about 5% by mass, the stirring was discontinued, and the residual pressure in the vessel was returned to ordinary pressure to complete the reaction. This aqueous dispersion was measured for the items described below. The results are shown in Table 1.

Solid matter concentration: This was determined based on the weight loss after an hour of drying of the aqueous dispersion obtained at 150° C.

Residual surfactant concentration: Nitric acid (1 g) was added to 100 g of the aqueous dispersion obtained, the mixture was stirred at 25° C. for 15 minutes, and the thus-obtained resin powder was again washed with 100 g of water and dried at 180° C. for 6 hours to give a PTFE powder. One gram of this powder was dispersed in 20 ml of methanol, and extraction was effected by stirring the dispersion at 50° C. for 24 hours. The concentration of the surfactant extracted into the methanol was determined by liquid chromatography/tandem mass spectrometry (LC/MS/MS) using Quattro LC (product of Micromass) and converted into the concentration in the resin.

In the above liquid chromatography, a Phenomonex Columbus C18 column (15 cm×2 mm i.d.), 0.02 M ammonium acetate:methanol (60:40 v/v, mobile phase A) and 0.02 M ammonium acetate:methanol (10:90 v/v, mobile phase B) were used, and elution was carried out using (1) a mobile phase A (100%)-to-mobile phase B (100%) concentration gradient during the period of 0 to 6 minutes after the start of elution, (2) the mobile phase B (100%) during the period of 6 to 12 minutes after the start of elution, and (3) a mobile phase B (100%)-to-mobile phase A (100%) concentration gradient during the period of 12 to 13 minutes after the start of elution. In the tandem mass spectrometry, the negative electrospray (ESP-) ionization method was employed.

Example 2

Preparation of a PTFE latex [2]

The polymerization and measurements were carried out in the same manner as in Example 1 except that 210 mg of the maleic acid half ester [HCF$_2$CF$_2$CF$_2$CF$_2$CH$_2$OOCCH=CH—COONH$_4$] obtained in Production Example 2 was used. The results are shown in Table 1.

Comparative Example 1

Preparation of a PTFE latex [3]

The polymerization and measurements were carried out in the same manner as in Example 1 except that 240 mg of perfluorooctanoate [PFOA] was used as the surfactant. The results are shown in Table 1.

TABLE 1

|  | Example 1 | Example 2 | Comparative Example 1 |
|---|---|---|---|
| Solid matter concentration (% by mass) | 5.1 | 5.3 | 5 |
| Residual surfactant concentration (ppm) | 0.1 | 0.06 | 28 |

From Table 1, it was found that the residual surfactant level was very low in Examples 1 and 2, in which the 2-acyloxycarboxylic acid derivative [(CF$_3$)$_2$C(OCOCF$_2$CF$_2$CF$_2$H)COONH$_4$] or the maleic acid half ester [HCF$_2$CF$_2$CF$_2$CF$_2$CH$_2$OOCCH=CH—COONH$_4$] was used, as compared with Comparative Example 1 in which the surfactant PFOA was used.

INDUSTRIAL APPLICABILITY

The method of producing a fluoropolymer according to the invention, which has the constitution described hereinabove, can efficiently produce a fluoropolymer having a very low residual surfactant content in the resins and having good physical properties with little discoloration. The fluoropolymer aqueous dispersion of the invention, which has the constitution described hereinabove, can allow the fluoropolymer to occur stably and can provide a fluoropolymer-based molding, a coating and so forth with good physical properties with little discoloration. The 2-acyloxycarboxylic acid derivative of the invention, which have the constitution described hereinabove, can be suitably used as a surfactant and so on. The surfactant of the invention comprises the 2-acyloxycarboxylic acid derivative(s) mentioned above and therefore has appropriate surfactant activity.

The invention claimed is:

1. A 2-acyloxycarboxylic acid derivative which is represented by the general formula (I):

$$(\text{Rf}^2)_b-\underset{(\text{OCORf})_d}{\overset{(\text{Rf}^1)_a}{\text{C}}}-\text{COOM} \quad (1)$$

wherein Rf$^1$ and Rf$^2$ are the same or different and each represents H, F, a fluoroalkyl group containing 1 to 20 carbon atoms or an ether oxygen-containing fluoroalkyl group containing 1 to 20 carbon atoms, Rf represents a fluoroalkyl group containing 1 to 20 carbon atoms or an ether oxygen-containing fluoroalkyl group containing 1 to 20 carbon atoms, M represents H, NH$_4$, Li, Na or K, a and b each represents an integer of 0 to 2 and d represents an integer of 1 to 3 provided that a, b and d satisfy the relation a+b+d=3; Rf$^1$, Rf$^2$ and Rf are the same or different.

2. The 2-acyloxycarboxylic acid derivative according to claim 1, wherein Rf$^1$ and Rf$^2$ are the same or different and each is $$\text{A(CF}_2)_j(\text{CH}_2)_p-$$

wherein A represents H or F, j represents an integer of 1 to 6 and p represents an integer of 0 to 3.

3. The 2-acyloxycarboxylic acid derivative according to claim 1, wherein Rf is $$\text{A(CF}_2)_n(\text{CH}_2)_m-$$

wherein A represents H or F, n represents an integer of 1 to 4 and m represents an integer of 0 to 3, or $$\text{A(CF}_2)_q[\text{CFX—CF}_2(\text{CH}_2)_r\text{O}]_t\text{CFX—}$$

wherein X represents F or CF$_3$, q represents an integer of 0 to 3, r represents an integer of 0 to 2, t represents an integer of 1 to 3 and A is as defined above.

4. The 2-acyloxycarboxylic acid derivative according to claim 1, wherein Rf$^1$ and Rf$^2$ are the same or different and each is $$\text{A(CF}_2)_u-$$

wherein A represents H or F and u represents an integer of 1 to 3, and Rf is $$\text{A(CF}_2)_w(\text{CH}_2)_y-$$

wherein A is as defined above, w represents an integer of 2 to 4 and y represents an integer of 0 to 1.

5. A surfactant which comprises the 2-acyloxycarboxylic acid derivative according to claim 1.

6. A method of producing a 2-acyloxycarboxylic acid derivative,
which comprises producing the 2-acyloxycarboxylic acid according to claim 1 by esterifying a 2-hydroxycarboxylic acid derivative represented by the general formula (5):

$$(\text{Rf}^2)_b-\underset{(\text{OH})_d}{\overset{(\text{Rf}^1)_a}{\text{C}}}-\text{COOM} \quad (5)$$

wherein Rf$^1$ and Rf$^2$ are the same or different and each represents H, F, a fluoroalkyl group containing 1 to 20 carbon atoms or an ether oxygen-containing fluoroalkyl group containing 1 to 20 carbon atoms, M represents H, NH$_4$, Li, Na or K, a and b each represents an integer of 0 to 2 and d represents an integer of 1 to 3 provided that a, b and d satisfy the relation a+b+d=3, and an alkanoyl compound represented by the general formula (6):

$$\text{RfCOZ} \quad (6)$$

wherein Rf represents a fluoroalkyl group containing 1 to 20 carbon atoms or an ether oxygen-containing fluoroalkyl group containing 1 to 20 carbon atoms, Z represents —OM$^1$ or Y (M$^1$ representing H, NH$_4$, Li, Na or K and Y representing F or Cl).

* * * * *